United States Patent [19] [11] 4,219,257
Slappey et al. [45] Aug. 26, 1980

[54] OPHTHALMIC ENDOTHELIAL MICROSCOPE

[75] Inventors: Thomas E. Slappey; Dan B. Capehart, both of Gainesville, Fla.

[73] Assignee: American Hospital Supply Corporation, Evanston, Ill.

[21] Appl. No.: 959,532

[22] Filed: Nov. 13, 1978

Related U.S. Application Data

[63] Continuation of Ser. No. 738,372, Nov. 3, 1976, abandoned.

[51] Int. Cl.² .......................... A61B 3/00; A61B 3/10
[52] U.S. Cl. .................................... 351/1; 351/6
[58] Field of Search ..................... 351/1, 6, 14, 16; 356/124, 372, 352

[56] References Cited
U.S. PATENT DOCUMENTS
2,607,270  8/1952  Briggs .................................. 356/372

Primary Examiner—John K. Corbin
Assistant Examiner—Rodney B. Bovernick
Attorney, Agent, or Firm—Larry N. Barger

[57] ABSTRACT

An ophthalmic endothelial microscope assembly capable of determining a predetermined dimension, namely the thickness, of the cornea portion of an eye of a living patient. The present assembly includes a casing having an illumination directing means including a plurality of optical elements disposed between an illumination source and an objective lens. Sighting means, also optically aligned with the illumination directing assembly, is further optically aligned with the objective lens so as to attain proper sighting of the predetermined portion of the eye. A focusing assembly includes a plurality of linkage elements drivingly interconnected to both a gauge member and the objective lens whereby manipulation of the focusing assembly causes proper positioning and focusing of the objective lens relative to the cornea of the eye under examination concurrently to activation of the gauge member so as to determine accurately the actual thickness or other predetermined dimension of the cornea.

1 Claim, 5 Drawing Figures

OPHTHALMIC ENDOTHELIAL MICROSCOPE

This is a continuation of application Ser. No. 738,372, filed Nov. 3, 1976, now abandoned.

BACKGROUND OF THE INVENTION

1. Field of the Invention

An ophthalmic endothelial microscope assembly capable of optical observation through a sighting assembly aligned with an objective lens simultaneously to gauging or determination of the thickness dimension of the cornea portion of the eye through manipulation of the focusing assembly to accomplish proper and required observation of the eye.

2. Description of the Prior Art

Medical science has for some years been capable of performing corneal transplants from donor material into the body of a living patient. For efficient accomplishment of this procedure human corneal donor material is required to be examined in order to determine generally its fitness for transplant. Among certain factors specifically required for examination is the thickness dimension of the cornea.

The examination of human corneal donor material before grafting has been limited generally to slit-lamp observation. The presence of endothelial folds and cornea guttata has been the criteria for deciding whether or not to use a cornea for transplantation. Staining with the vital dyes, trypan blue and lissamine green, have been suggested as more accurate methods for assessing donor endothelial viability. These tests, however, have generally been performed on the excised donor button and may require irrigation of the endothelium.

An ophthalmic endothelial microscope assembly developed by Dr. David Maurice, PhD, has previously offered a new means of critical examination of corneal donor material while the globe remains intact. With this structure corneal thickness and thickness of the individual layers was capable of measurement to within generally desirable ranges at various points along the cornea. Advantages of this prior art system includes examination of the cornea portions while the globe is intact thereby eliminating the need of exposure of the corneal endothelium or the handling or washing thereof.

However, this prior art structure of Maurice was generally limited to observation and examination of the eye after removal from the human or animal donor.

Subsequent to the introduction of the Maurice ophthalmic endothelial microscope assembly, structural modifications were made to this structure which allowed for the observation and photographing of the corneal endothelium in live patients. The later developed method was suitable for animal experimentation and for diagnostic observation in clinical research in humans. While this apparatus described a method for the direct microscopic visualization of the corneal endothelium in vivo and further provided for the recording of the image photographically, certain means contained in the structure did not accomplish maximum efficiency relative to capabilities for accurately gauging the thicknes of the cornea.

Accordingly, there is a recognized need in this particular area of medical science for the accurate examination, observation and more specifically measurement of the thickness of the corneal emdothelium. This measurement, as generally set forth above, is requisite in the determination of proper condition of the cornea to insure that the endothelium is free from those morphological changes in the cells of the endothelium associated with age, inflammation and ocular disease. Previous to the invention described herein information correlating this morphological changes with abnormal physiological function in live patients has been limited.

SUMMARY OF THE INVENTION

This invention relates to an ophthalmic endothelial microscope of the type designed to measure predetermined dimensions and specifically thicknesses of the cornea in a living patient.

The microscope comprises a casing having a light source attached to the exterior thereof or alternately on the interior of the casing, and positioned to direct radiation to the objective lens means through the interior of the casing along a defined path of travel of light. Illumination directing means is mounted on the interior of the casing and disposed in predetermined disposition relative to the light source and the objective lens means.

The objective lens means is mounted to provide viewing through to the exterior of the casing and comprises an objective lens element and positioned substantially adjacent the point of examination and/or contact with the eye under examination. In this embodiment the illumination directing means comprises a plurality of optical elements disposed in spaced apart relation to one another and defining the path of travel of illumination or radiation from the light source to the objective lens means. Light directed through the objective lens means onto the cornea or eye portion being examined allows for proper viewing as will be explained in greater detail hereinafter.

The plurality of optical elements comprising the illumination directing means include a first and second primary prism disposed in aligned, spaced apart relation to one another and positioned to direct the radiant energy from its source along a predetermined path through the casing to a point substantially in the path of viewing and in aligned relation to the objective lens means. More specifically, a third optical element of the plurality of optical elements which comprise the illumination directing means includes an objective prism disposed in substantially axially aligned relation with the objective lens means and specifically disposed in aligned relation with the second of the primary prisms and between the objective lens and this second primary prism. Accordingly, light is directed from the first and second primary prism to the objective means by the disposition of the objective prism.

The ophthalmic endothelial microscope of the present invention further comprises sighting means including an eye piece in substantially linear or axial alignment with the objective lens means and the portion of the path of travel of radiation as it is directed from the objective prism through the objective lens to the portion of the eye being examined. As generally set forth above, the sighting means includes the eye piece mounted in aligned relation with the objective lens means and in communicating relation with the exterior of the casing so that the line of sight or channel of vision is established between the eye of the viewer and the eye of the patient under examination.

Focusing means is further included in the subject invention and is mounted on the casing. The focusing means includes an operative element which is available to the exterior of the casing and configured for hand manipulation. The focusing means further comprises linkage element interconnected between the operative element and the objective means and, in the preferred embodiment, includes a substantially elongated shaft. The elongated shaft is movably interconnected and drivingly engages the objective means through a plurality of ear elements disposed in intermeshing relation to one another. The opposite end of the shaft is connected to the operative element by a gear assembly which causes rotation of the shaft about its own longitudinal axis upon rotation of the operative element. This rotation of the shaft in turn causes rotation of the objective lens means and proper focusing along the line of sight defined by the sighting means.

A gauge means is further provided in the structure of the subject invention and is disposed in driven, activating relation to the operative element. Accordingly, manipulation of the operative element simultaneously causes movement of the linkage means so as to position the objective lens means for proper focusing and distancing relative to the eye of the patient under examination. At the same time, the same movement of the operative element serves to activate or operate the gauge means thereby determining the amount of displacement of the objective means which in turn provides accurate indication of predetermined dimensions, such as thicknesses, of the cornea itself.

Other structural features of the present invention include a gross focusing assembly mounted on the exterior of the casing and disposed in interconnecting relation between the casing and any support base on which the casing is mounted. Further adjustment means are interconnected between the casing itself and at least one of the plurality of optical elements defining the illumination directing means.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 2:
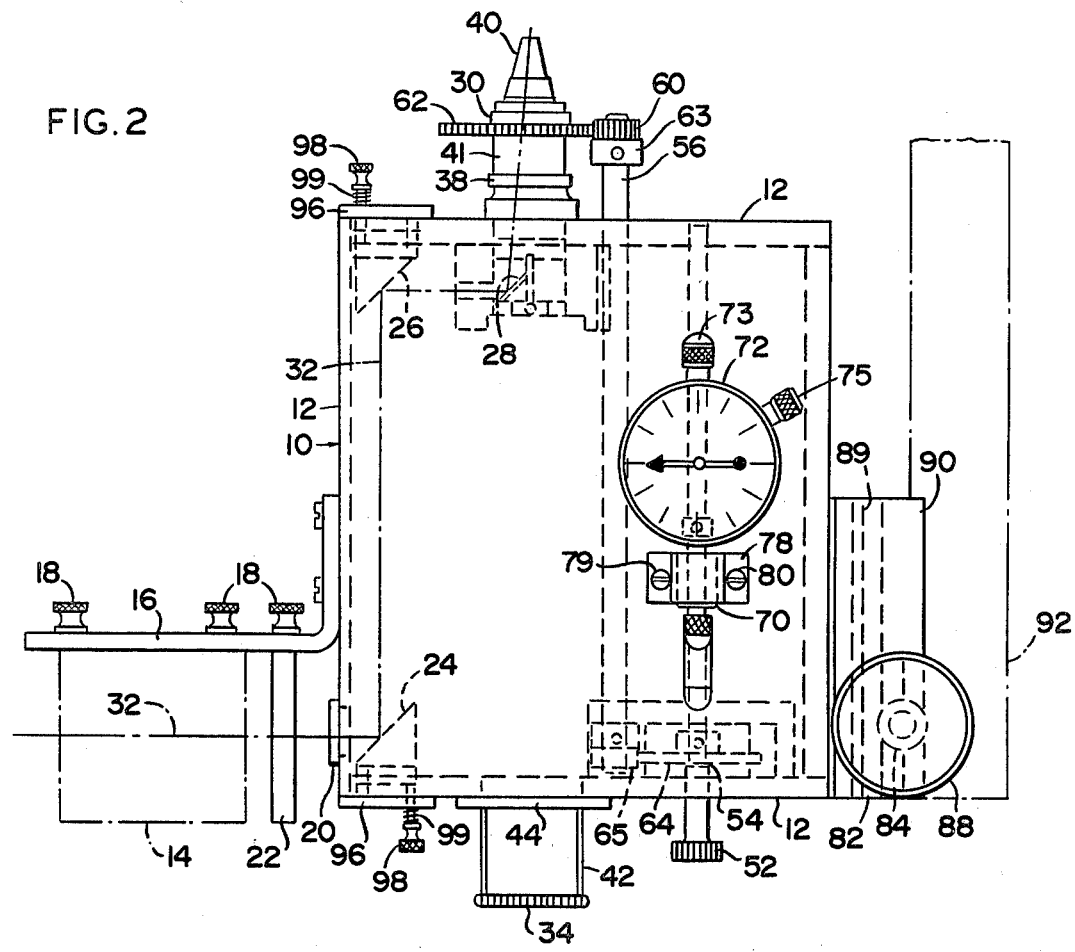
FIG. 2 is a side view of the embodiment of FIG. 1 showing details and the relative disposition of the gauge means on the exterior portion of the casing.
Figure 1:
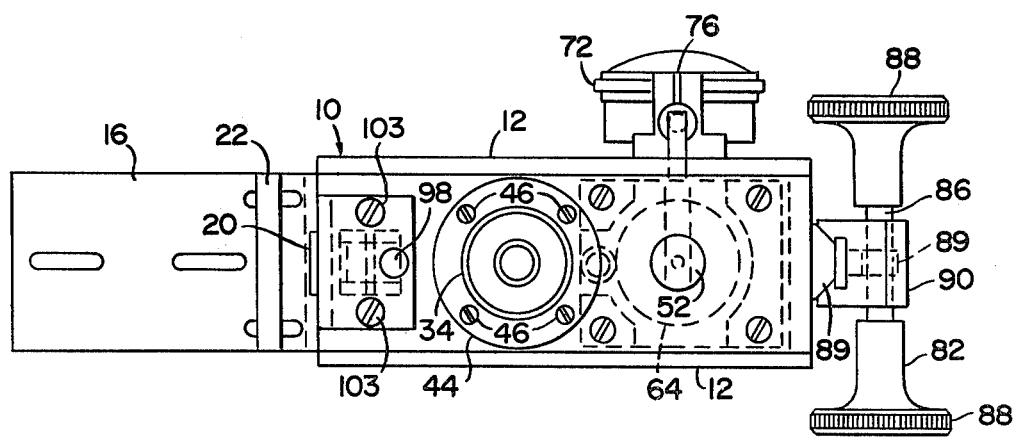
FIG. 1 is an end view of the ophthalmic endothelial microscope of the present invention.

As shown in FIGS. 1 and 2, the ophthalmic endothelial microscope of the present invention is generally indicated as 10 and comprises a casing 12 having a light source generally indicated as 14 and represented in broken lines disposed on the exterior thereof and connected thereto by mounting brackets 16 having adjustable connecting means 18 serving to adjustably position the light source 14 in proper position relative to the casing and its entrance aperture 20. A slit shield 22 serves to break down the path of illumination from the light source 14 in a more precise beam as it enters aperture 20 into the interior of the casing 12.

An illumination directing means comprising a plurality of optical elements 24, 26 and 28 are disposed in spaced relation to one another so as to define the path of travel of the illumination from its source 14 on the exterior of the casing to the objective lens means generally indicated as 30. More specifically, the optical elements 24 and 26 comprise primary prisms disposed in linearly aligned spaced relation to one another and specifically located to direct the path of illumination represented by axis line 32 from the light source 14 to the third optical element 28. This third optical element is structured in the form of a prism and is hereby termed an objective prism due to its optically aligned disposition relative to the objective lens means 30 and the line of sight defined by the sighting means generally indicated as 34.

Therefore, the objective prism 28 serves to at least partially define the path of illumination from the primary prisms 24 and 26 through an objective lens 38 of the objective lens means 30 to the eye under examination (not shown) through cone lens 40 which is brought into actual engagement with the exterior surface of the eye for proper measurement of the cornea dimension as set forth above. The objective lens 38 and the cone lens 40 are disposed within a sleeve like housing 41 in spaced apart but visually aligned relation to one another along a substantially common axis.

Further, the sighting means generally indicated as 34 comprises an eye piece 42 secured to the exterior of the casing 12 by a mounting ring 44 and conventional connectors 46. Lens aperture 48 allows for proper viewing along a substantially linear path in optically aligned relation with the objective lens 38 and cone lens 40 of the objective lens means 30. Since light is directed efficiently through the objective lens means 30 by the provision and alignment of the objective prism 28, proper viewing therethrough and examination of the eye of the patient disposed adjacent to the cones lens 40 can be accomplished.

The ophthalmic endothelial microscope of the present invention further comprises a focusing means including operative element 52 accessible from the exterior of casing 12 and specifically designed and configured for hand manipulation to accomplish movement thereof. The operative element 52 engages gear assembly generally indicated as 54 which drivingly interconnects and causes to rotate the elongated shaft 56 serving as one of the plurality of linkage elements. These linkage elements and in particular the shaft 56 movably interconnects the operative element 52 with the objective means 30. The linkage elements further include a plurality of gears 60 and 62 fixedly attached to one end of the shaft element 56 and about the objective lens 38, respectively. A connecting collar 63 serves to attach and properly position the gear elements 60 to the end of the shaft 56. Therefore, rotation of the shaft 56 due to hand manipulation of the operative element 52 causes a rotation and thereby focusing of the objective lens 38 due to the rotatable, intermeshing engagement between gear elements 60 and 62. Similarly, the gear elements 64 and 65 serve to drivingly interconnect the operative element 52 to the opposite end of shaft 56 relative to that drivingly attached to the objective lens means 30.

Gear means generally indicated as 70 also serves to drivingly interconnect and activate a gauge means 72 upon manipulation of the operative element 52 and displacement of the objective lens means 30 and dip cone 40 relative to the eye being examined. The gear means 70 serves to interconnect the operative element so that the operative element will concurrently or simultaneously drive both the shaft means 56 thereby causing focusing of the objective lens means 30 and at the same time actuate the gauge means 72. Proper and/or conventional stop and go or switch elements 73 and 75 are interconnected to the gauge means 72 so as to control the operation and/or positioning of indicating dials 76. A mounting bracket 78 attached to the exterior of the casing 12 by substantially conventional connectors 79 and 80 serves to house at least a portion of the gear means generally indicated as 70 calling for the interconnection between the gauge means 72 and the operative element 52.

Focusing means further comprises a gross focus assembly generally indicated as 82 which includes a rack and pinion gear means including pinion gear member 84 mounted on shaft 86 and driven by knobs 88 in a conventional manner. The pinion gear 84 is disposed in intermeshing and movable relation to the rack gear 89 wherein both are disposed within the housing or surrounding frame portion 90.

This gross focusing assembly is disposed in interconnecting relation so as to supportingly mount the casing 12 on some type of base or supporting surface 92 which is relatively fixed and which allows for the overall orientation or proper postioning of the casing 12 relative to the patient or area of examination whereat the patient is positioned.

Figure 3:
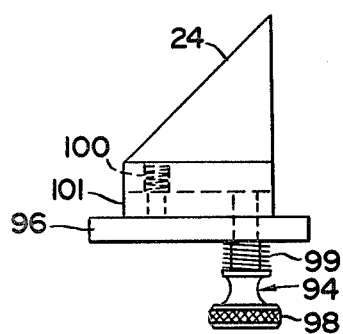
FIG. 3 is a detail view of the adjusting means and one of the optical elements comprising the illumination directing means.

Further structural features of the present invention comprise (FIGS. 2 and 3) the mounting of the optical elements 24 and 25 including an adjustment means generally indicated as 94 (FIG. 3) and secured to a mounting base 96. Operable element 98 in the form of a conventional knob or the like is spring biased against the mounting base 96 by means of spring 99 which serves to normally bias the operable element 98 outwardly away from the base 96. Similarly, an adjusting spring 100 is disposed between a flange 101 of the support base 96 and the primary prism 24 itself. Again, manipulation of the operable element 98 by the hand serves to minutely adjust the position or orientation of the prism 24 relative to the defined path of travel of the light entering the casing 12 from the light source 14 and through the slit shield 22. For the purpose of clarity only a single adjustment structure was defined but it should be made clear and is obvious through the representation of FIG. 2 that both such optical elements 24 and 26 have a similarly structured adjustment means.

With reference to FIG. 1 the supporting base 96 may be fixedly attached to the exterior portion of the casing as shown by a plurality of connector elements 103.

Figure 4:
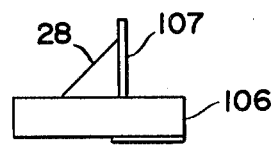
FIG. 4 is a detail view of the embodiment of the objective prism disposed in optically aligned relation between the remaining optical elements of the illumination directing means and the objective lens itself.

With reference to FIG. 4 a support base 106 is mounted on the interior of the casing serves to support the objective prism 28 therein by means of support platform 107 attached thereto.

Figure 5:
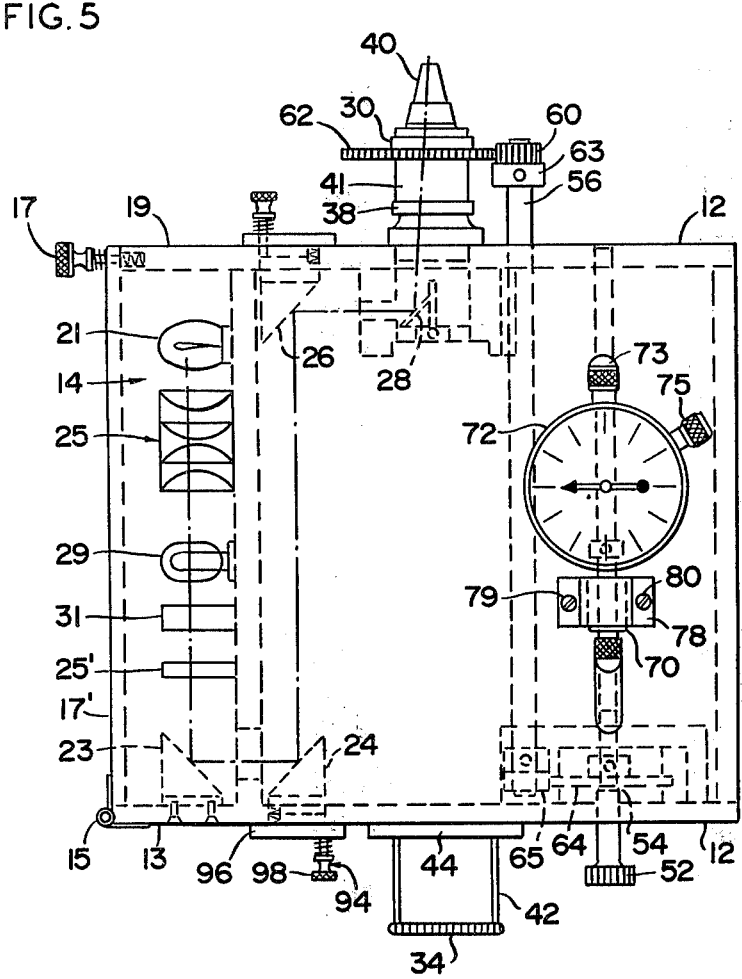
FIG. 5 is a side view, in partial section, of another embodiment of the present invention wherein the light source is mounted on the interior of the casing.

FIG. 5 represents another embodiment of the present invention wherein the illumination source generally indicated as 14 is mounted on the interior of the casing in a substantially upper portion generally indicated as 13. A substantially conventional hinge element 15 serves to interconnect a lid portion 17 to the upper portion 13 of the casing. A lock screw 17 serves to secure the opposite end of the lid portion 17 to the remainder of the casing as at 19. Accordingly, clear access is provided to the interior of the upper portion of the casing 13 for replacement or repair of the various components which comprise the light source 14.

In the embodiment shown, the light source specifically comprises light bulb element 21 disposed in aligned relation to fixed prism element 23. In this particular embodiment, the illumination directing means comprises the fixed prism element 23 which may be arranged in aligned relation with the bulb 21 in a manner so as to have the illumination issuing therefrom focused thereon by means of a plurality of focusing lens elements generally indicated as 25.

An alternate source of illumination comprises a flashbulb 29 also mounted in the upper portion of the casing 13 and in general alignment with the fixed prism 23 through the focusing lens element 25' and the adjusting light slit element 31.

Also as clearly shown in FIG. 5, the fixed prism element 23 is disposed above, and in spaced but optically aligned relation to the adjustable prism element 24. The remainder of the illumination directing means including the placement of the two adjustable prism elements 24 and 26. In addition, the second fixed prism element referred to as the objective prism 28 is disposed in aligned relation with the adjustable prism elements 24 and 26 as previously explained with reference to the embodiment of FIG. 2.

It will thus be seen that the objects set forth above, among those made apparent from the preceding description, are efficiently attained, and since certain changes may be made in the above article without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An opthalmic microscope for examining an eye of a living patient whose head is rigidly fixed, comprising: a base with a generally horizontal track; a casing mounted on the track of the base for coarse horizontal movement relative to the base; said casing being generally rectangular in shape with top, bottom, front, rear, and side walls, and having a width that is substantially smaller than its height, whereby substantially the entire casing can be positioned to one side of a patient's nose during examination of an eye while leaving the other eye available for focusing on a wall chart or the like; an objective lens mounted on the front wall of the casing; a viewing lens mounted on the rear wall of the casing so that the line of sight between the viewing and objective lenses is generally horizontal; a light source mounted on the casing's top wall, which light source has a width eqaul to or less than the casing's width so that the light source does not interfere with the patient's anatomy; a first prism in the casing adjacent a rear wall of the casing; a first adjustable screw connected to the first prism and protruding through the casing for angularly adjusting the first prism; a second prism in the casing adjacent a front wall of the casing; a second adjustable screw connected to the second prism and protruding through the casing for angularly adjusting the second prism; said first and second prisms being located in the casing above the line of sight between viewing and objective lenses; a third prism located in the casing below the second prism to direct light through the objective lens; a driven gear mounted on an exterior of the objective lens to rotatably adjust the objective lens for fine focusing; a driving gear meshing with the driven gear of the objective lens, the driving gear being substantially smaller in diameter than the driven gear; a shaft extending through the casing along an axis generally parallel and located below the line of sight between the viewing and objective lens, a front end of the shaft being connected to the driving gear, and a rear of the shaft being connected to a knob outside the casing so that the shaft and gears do not increase the width of the casing; a gauge mounted on one side wall of the casing and this gauge is operatively connected to the shaft to record movement of the objective lens through the shaft movement.

* * * * *